US009988591B2

(12) United States Patent
Diez et al.

(10) Patent No.: US 9,988,591 B2
(45) Date of Patent: Jun. 5, 2018

(54) PERFUME COMPOSITIONS

(71) Applicant: CHANEL INC, New York, NY (US)

(72) Inventors: Ricardo Diez, Piscataway, NJ (US); James Giblin, Piscataway, NJ (US)

(73) Assignee: CHANEL INC, New York, NY (US)

( * ) Notice: Subject to any disclaimer, the term of this patent is extended or adjusted under 35 U.S.C. 154(b) by 110 days.

(21) Appl. No.: 15/098,543

(22) Filed: Apr. 14, 2016

(65) Prior Publication Data

US 2017/0298290 A1 Oct. 19, 2017

(51) Int. Cl.

*A61K 8/18* (2006.01)
*A61K 8/00* (2006.01)
*C11B 9/00* (2006.01)

(52) U.S. Cl.

CPC .......... *C11B 9/0061* (2013.01); *C11B 9/0019* (2013.01); *C11B 9/0034* (2013.01); *C11B 9/0053* (2013.01)

(58) Field of Classification Search

USPC ....................................... 512/17, 16, 14, 8, 1
See application file for complete search history.

(56) References Cited

U.S. PATENT DOCUMENTS

| | | | | |
|---|---|---|---|---|
| 5,374,614 A | | 12/1994 | Behan et al. | |
| 5,681,552 A | * | 10/1997 | Shevade .............. | A61K 8/0229 424/65 |
| 6,803,050 B2 | | 10/2004 | Denzer et al. | |
| 7,655,613 B2 | | 2/2010 | Vlad et al. | |
| 8,461,099 B2 | * | 6/2013 | Fraser .................... | A61K 8/068 512/14 |

OTHER PUBLICATIONS

T. J. Lin, "Surfactants in Cosmetics", Surfactants Science Series, vol. 16, (1985), 29-52, New York, NY USA.

* cited by examiner

*Primary Examiner* — Jessica Whiteley
(74) *Attorney, Agent, or Firm* — Young & Thompson

(57) ABSTRACT

An ethanol-free perfumed composition includes a fragrance and:

a) at least one crypto anionic surfactant,
b) at least one ethoxylated nonionic surfactant having a molecular weight greater than 1700 containing at least 40% of ethylene oxide,
d) at least one glycol having from 3 to 8 carbon atoms, and
e) water;

wherein the weight ratio of the fragrance to the surfactants and glycols is from 1/1 to 1/6.

20 Claims, No Drawings

PERFUME COMPOSITIONS

FIELD OF INVENTION

The present invention relates to ethanol-free perfumed compositions suitable for leave-on cosmetics, said compositions being clear, transparent and stable during storage. The invention is also directed to ethanol-free perfumed products obtainable by dilution in water of ethanol-free perfume preparations.

BACKGROUND OF THE INVENTION

Historically, perfumes have been prepared by dissolving fragrance oils in volatile alcohols, primarily ethanol, or in a mixture of ethanol and water. The industrialization of surfactants and the advances in colloid science have made possible the solubilization of fragrances in water by means of emulsification with surfactants. When an emulsion has a particle size of about 140 nm or less it is referred to as a microemulsion. The small size of these microemulsions containing fragrance oils results in perfume products that are clear or almost clear, and are not very different in appearance to conventional ethanol-based perfumes.

Microemulsions contain physical structures which can be described as swollen micelles, inversed micelles or continuous bi-layers. None of these structures are present in conventional ethanol-based perfume products.

The key benefit of water-based perfumes is a reduction in VOC's (Volatile Organic Compounds). Another benefit is the immediate perception of the intrinsic nature of the fragrance oils due to the absence of ethanol or ethanol-like alcohols. However, microemulsion water-based products tend to be foamy, sticky or even irritating to the skin due to presence of the surfactants required to solubilize the fragrance.

These drawbacks are magnified as the surfactant content increases. This content depends on the intrinsic efficiency of the selected surfactant system, the ease or difficulty of solubilization of the fragrance oil itself, and the total content of the fragrance oil in the final perfume product. In any case, T. J. Lin mentioned in Surfactants in Cosmetics, Surfactants Sci. Ser. Vol. 16, (1985), 29-52, that the practical preparation of these microemulsion products will need a ratio of surfactant solubilizer system to fragrance oil much greater than 1/1. There is therefore a need to make the microemulsions with low concentrations of skin compatible surfactants.

U.S. Pat. No. 5,374,614 discloses low VOC microemulsions for perfumery applications with reduced surfactant content. The surfactant system consists of a non-ionic fraction and an anionic fraction, which are also representative of other disclosures in the art, such as in U.S. Pat. No. 7,655,613

The non-ionic fraction in these documents is based on ethoxylated surfactants that are known for their excellent fragrance solubilization properties. Both patents disclose a long list of ethoxylated compounds. However, ethoxylated surfactants with molecular weights in the 400 to 1200 range and based on fatty acids, fatty alcohols, and even the alkyl phenol as disclosed in U.S. Pat. No. 5,374,614 and no longer used in consumer products, are known to disrupt the lipids of the stratum corneum. While acceptable for usage in many consumer and industrial products, where they may have functions in addition to fragrance solubilization, these surfactants are not very suited for perfume products for application to the skin or hair. Ethoxylated non-ionic surfactants with high molecular weight, such as the ethoxylated castor oil materials disclosed in U.S. Pat. No. 8,461,099, are very suited for perfumes for personal use.

The anionic surfactants disclosed in these patents are also known for their use in many personal cleansing products, household products, laundry products and detergent products in general. They are known to negatively interact with the corneocites of the skin to cause irritation, especially when left deposited on the skin, as it is the case of perfumery products intended for personal use.

Anionic surfactants are required in microemulsion-based fragrance products to offset the negative impact that the fragrance has on the cloud point of ethoxylated non-ionic surfactants. Non-ionic ethoxylates exhibit inverse water solubility behavior since they are less soluble as the temperature of the solution is raised. The temperature at which they are no longer soluble in water is called the cloud point. In the absence of fragrance, most of the ethoxylated materials disclosed in the prior art have cloud points above 50° C., but in the presence of solubilized fragrance the cloud point may be lowered to below 40° C., resulting in a product that may be hazy within the range of product usage or storage. The incorporation of anionic surfactants raises the cloud point above 40° C. in well balanced systems from a chemical viewpoint.

There is a need therefore to identify new surfactant systems capable of maintaining the cloud point of the water-based fragrance products above 40° C., while remaining clear down to 5 C, and with minimal or no irritation the skin, and reduced foaming and stickiness.

The present invention provides an unexpected and advantageous solution to all these requirements with the incorporation of skin compatible crypto-anionic surfactants that totally replace the anionic materials described as indispensable in the prior art.

An object of the present invention is therefore to provide new leave-on ethanol-free perfumed compositions which are stable to storage, in particular remain clear between 5 and 40° C. and which are non-irritant to the skin.

SUMMARY OF THE INVENTION

The present invention relates to ethanol-free perfumed compositions containing water in replacement for ethanol, comprising a combination of two types of surfactants, namely ethoxylated crypto-anionic surfactants and ethoxylated non-ionic surfactants, and glycol(s). The specific amount of each component is adjusted in the microemulsion to accommodate the solubilization of the fragrances used in perfumed composition, which are very complex and diverse in composition.

In this respect, the present invention pertains to an ethanol-free perfumed composition comprising a fragrance and:

a) at least one crypto anionic surfactant, b) at least one ethoxylated non-ionic surfactant having a molecular weight greater than 1700 containing at least 40% of ethylene oxide, d) at least one glycol having from 3 to 8 carbon atoms, and e) water;

wherein the weight ratio of the fragrance to the surfactants and glycols is from 1/1 to 1/6.

The present invention is also directed to a perfumed composition obtainable by admixing in situ:

an ethanol-free perfumed preparation comprising a fragrance and:

a) at least one crypto anionic surfactant, b) at least one ethoxylated non-ionic surfactant having a molecular weight greater than 1700 containing at least 40% of ethylene oxide, d) at least one glycol having from 3 to 8 carbon atoms, and e) water;

wherein the weight ratio of the fragrance to the surfactants and glycols is from 1/1 to 1/6 and water.

The invention is also directed to an ethanol-free perfume product in a kit form comprising two compartments in which at least the following ingredients are divided:

a fragrance at least one crypto anionic surfactant, at least one ethoxylated non-ionic surfactant having a molecular weight greater than 1700 containing at least 40% of the ethylene oxide, at least one glycol having from 3 to 8 carbon atoms;

wherein the weight ratio of the fragrance to the surfactants and glycols is from 1/1 to 1/6, and water, wherein the compartment that contains the fragrance does not simultaneously contains the water.

This invention also pertains to the use of at least one crypto anionic surfactant and at least one non-ionic surfactant having a molecular weight greater than 1700 containing at least 40% of oxyalkylene units, to solubilize fragrances in an ethanol-free perfumed composition.

It is indeed of the merit of the inventors to have discovered that the combination of specific crypto-anionic surfactants with specific non-ionic surfactants comprising oxyalkylene units made it possible to provide clear, transparent and storage stable ethanol-free perfume compositions that are perfectly non-irritant to the skin.

DETAILED DESCRIPTION OF THE PREFERRED EMBODIMENTS

Ethanol-free Composition

Ethanol-free perfumed composition are formulations which are substantially free of ethanol, preferably containing less than 3% of ethanol, more preferably less than 2% and even more preferably less than 1% of ethanol.

Microemulsion

The perfumed compositions of the present invention can preferably be in the form of a microemulsion.

Within the meaning of the invention, the term "microemulsion" is intended to designate emulsions wherein the dispersed phase is in the form of droplets of average particle size below 140 nm.

As used therein, the term "microemulsion" denotes a thermodynamically stable, macroscopically homogeneous mixture of fragrances (oils), water and surfactant. It contains, on a microscopic level, individual domains of oil/fragrances and water separated by a surfactant layer.

Microemulsions may be distinguished from solutions in that they comprise more than one phase; they are microstructured and may contain "oil"-swollen micelles, a bicontinuous structure, water-swollen inverse micelles or other structures depending on the amount of "oil" in the system. True solutions show none of these microstructural characteristics.

Fragrances

As mentioned above, the perfumed compositions of the present invention comprises at least one fragrance.

In the context of this specification the term "fragrance" is understood as referring to one or a mixture of olfactively active materials providing a pleasant smell. Mixture of fragrances can be referred to as "fragrance composition". The term fragrance is taken to mean any individual material which may be an ingredient of a fragrance composition even though that perfume ingredient may itself comprise many individual chemical compounds. In a general manner these ingredients belong to chemical classes as varied as terpene hydrocarbons, acetates, alcohols, aldehydes, ketones, esters, ethers, nitriles, nitrogenous or sulfurous heterocyclic compounds and essential oils of natural or synthetic origin. The "fragrance" of the invention can be any natural oil or extract, or chemical compound used in a fragrance composition. A more detailed description is not warranted here since skilled persons are familiar with the ingredients and able to select them according to the nature of the product to be perfumed and the desired olfactory effect.

Water solubility of the fragrances is inversely correlated with the theoretical octanol/water partition coefficient usually expressed in the logarithm as "log P octanol/water" or "log Pow". Low log Pow values indicate more water soluble molecules while higher log Pow values are indicate a more hydrophobic compound. However, the log Pow characterizes fragrances in a chemical environment free of surfactants. When surfactants are present, the log Pow may only provide a partial description of the fragrance intrinsic solubility that is now governed by the incorporation of the fragrance ingredients into the various sites of the surfactant micelles.

Fragrance may be used pure or may also include solvents used at levels up to 30% of the fragrance. Solvents are defined as relatively low odor liquids which can dissolve target material in reasonable proportions. Some of the common solvents used in perfumery such as propylene glycol and dipropylene glycol are water miscible; as such they may assist in dissolving a fragrance into a clear aqueous solution or microemulsion. For the purposes of this specification, proportions of fragrances are quoted excluding any water miscible solvent which may be present.

In one embodiment, the perfumed compositions of the invention contain from 1% to 20% by weight of one or more fragrances, preferably 2.5% to 15% by weight, more preferably 3% to 10% by weight of fragrances

Crypto-anionic Surfactant

The ethanol-free perfumed composition of the invention also comprises at least one crypto-anionic surfactant.

Crypto-anionic surfactants are defined, within the meaning of the invention, as surfactants that behave like non-ionic or anionic depending on the pH conditions. This description is consistent with U.S. Pat. No. 6,803,050. Generally speaking, crypto-anionic surfactants are mainly in a non-ionic state when the pH of the medium is below 3. As the pH of the medium increases, the surfactant becomes more anionic. Generally speaking also, within the pH range of the medium required for perfumed compositions, crypto-anionic surfactants contain a mixture of non-ionic and anionic species. Also, and unlike conventional anionic surfactants, crypto-anioinic surfactants are compatible with cationic surfactants in a broad pH range.

In a preferred embodiment, the crypto anionic surfactant is flanked by a citrate or phosphate group or a mixture of them.

The preferred crypto-anionics in this invention correspond to the families of citrate esters and organophosphates, also known as phosphate esters, and are made by partial esterification of a non-ionic ethoxylated material with an esterifying agent.

In a preferred embodiment, the crypto anionic surfactant is derived from an ethoxylated non-ionic material having at least 30% of ethylene oxide attached to an alkyl, aryl, or propoxy chain or a mixture of them.

The hydrophobe part of the non-ionic ethoxylated material can be a linear alkyl chain, or a branched alkyl chain, or an unsaturated alkyl chain, or an aryl chain, or a polymerized propylene oxide chain. The degree of ethoxylation of the hydrophobe part must be least 30% EO by weight, preferably 30 to 70%. For the purpose of this specification, EO refers to the content of the hydrophilic ether group from the precursor material ethylene oxide, and it will be expressed as % EO or number of moles EO.

The esterification of the non-ionic ethoxylated material can be conducted with citric acid to form the citrates esters or with polyphosphoric acid, phosphorous pentoxide or phosphorous oxychloride to form the phosphate esters.

In a preferred embodiment, the crypto anionic surfactant is an ester having at least one non esterified acid group.

A partial esterification is conducted to prevent the formation of triester and obtain variable mixtures of monoester and diester compounds and to have at least one unreacted acid group available for further neutralization with an inorganic or organic base. Triesters are undesirable due to poor water solubility and because they prevent the presence of the necessary unreacted acid group.

The unreacted acid group is finally neutralized, totally or partially, with alkaline materials like sodium and potassium hydroxides or with typical organic bases, mainly amines. The neutralization can be measured by pH and adjusted as required, normally in the range 4.5 to 8.0

This neutralization with a base changes the nature of the surfactant from a mainly non-ionic to a more anionic state.

Non limiting examples of suitable crypto anionic surfactants include the citrate ester of laureth-7 (INCI name: laureth-7 citrate) such as the one commercialized by BASF under the reference Plantaplon LC 7, and the phosphate ester of oleth-10 (INCI name: Oleth-10 Phosphate) commercialized by Croda as Crodafos 10A-SS, and the phosphate ester of phenol-6 EO (INCI name: Phenol-6 EO Phosphate) also from Croda (Crodafos PH6A-LQ), and the phosphate ester of PPG-5 Ceteth-10 (INCI name: PPG-5-ceteth-10 phosphate) also from Croda (Crodaphos SG-LQ).

In a preferred embodiment, the crypto anionic surfactant is chosen from:

the citrate ester of laureth-7, and the phosphate ester of PPG-5 Ceteth-10 and mixtures thereof.

In one embodiment, the perfumed, aqueous compositions of the invention contain from 0.1 to 10% by weight of a crypto anionic surfactant, preferably from 1% to 5% by weight, relative to the total weight of the composition.

In a preferred embodiment, the weight ratio of crypto anionic to non-ionic surfactants is in the range of 1/1 to 1/7, depending on the fragrance oil.

Ethoxylated Non-Ionic Surfactant

The ethoxylated non-ionic surfactant fraction in this specification must be made of materials having an individual molecular weight larger than 1700, and containing at least 40% EO.

The first type of the preferred ethoxylated non-ionic materials is based on castor oil, hydrogenated or not, containing at least 40% EO, preferably from 50 to 75% EO. Their general INCI name is PEG-X (Hydrogenated) Castor Oil, where "X" indicates the number of moles of EO.

They are manufactured, among others, by Croda under the trade name Croduret. The preferred surfactants are liquid or very soft solids that dissolve easily with the fragrance oil or the glycol phase with no significant heat applied. Preferred surfactants are PEG-25 Hydrogenated Castor Oil, molecular weight of about 2000, and about 55% EO (Croduret 25); PEG-40 Hydrogenated Castor Oil, molecular weight of about 2660, and about 66% EO (Croduret 40 LD); and PEG-50 Hydrogenated Castor Oil, molecular weight of about 3100, and about 71% EO (Croduret 50 SP).

Other preferred ethoxylated non-ionic surfactants are known as "block copolymers". They consist of a central hydrophobic block made of polymerized propylene oxide (PO) flanked by two blocks of polymerized ethylene oxide (EO) to improve water solubility. These materials have the general INCI name of Poloxamer.

The ethoxylated block copolymer has a molecular weight from 2500 to 35000 and containing from 60% to 75% oxyethylene units.

They are manufactured, among others, by BASF under the trade name Pluronic. The preferred surfactants are Pluronic L35, L44 and L46, all liquid, with a molecular weight above 1800 and more than 50% EO. The most preferred is Pluronic L64, with a molecular weight of about 2900 and 70% EO. The INCI name is Poloxamer 184.

Another preferred ethoxylated non-ionic material is a blend of PPG-26-Buteth-26 with PEG-40 Hydrogenated Castor Oil. It is manufactured by Sensient under the trade name of Solubilizer LRI.

In one embodiment, the perfumed, aqueous compositions of the invention contain from 1 to 20% by weight of a nonionic surfactant, preferably from 1% to 10% by weight, relative to the total weight of the composition.

Glycol

The ethanol-free perfumed composition of the invention also comprises at least one glycol having from 3 to 8 carbon atoms, preferably 5 to 6 carbon atoms.

The glycol or glycol(s) of the invention are preferably aliphatic diols with vicinal or non vicinal hydroxyl groups.

Suitable glycols with vicinal diols having 3 to 8 carbon atoms include 1,2-pentanediol, 1,2-hexanediol, 1,2-heptanediol or 1,2-octanediol. Suitable glycols with non vicinal diols having 4 to 8 carbon atoms include butylene glycol, pentylene glycol, isopentyl glycol, hexylene glycol, dipropylene glycol (which is a mixture of three isomers, 4-oxa-2,6-heptandiol, 2-(2-hydroxy-propoxy)-propan-1-ol, and 2-(2-hydroxy-1-methyl-ethoxy)-propan-1-ol) or octylene glycol.

In a preferred embodiment, glycol having from 3 to 8 carbon atoms can be chosen from pentylene glycol, isopentyldiol; 1,2-hexanediol; hexylene glycol and dipropylene glycol or a mixture thereof.

In one embodiment, the weight ratio of the total surfactants to the glycols is in the range of 4/1 to 1/1.

In a further embodiment, the weight ratio of the fragrances to the surfactants and glycols is adjusted in the range of 1/1 to 1/6. This ratio should be as close as possible to 1/1 to minimize foaming, stickiness and irritation.

Water Phase

The perfumed compositions of the present invention comprise at least 50% by weight water. In one embodiment, the compositions comprise from 60% to 99% by weight water. In a further embodiment, the compositions comprise from 65% to 85% by weight water.

For the preparation of a perfumed composition by admixing in situ:

an ethanol-free perfumed preparation comprising a fragrance and:

a) at least one crypto anionic surfactant, b) at least one ethoxylated non-ionic surfactant having a molecular weight greater than 1700 containing at least 40% of the ethylene oxide, d) at least one glycol having from 3 to 8 carbon atoms;

wherein the weight ratio of the fragrance to the surfactants and glycols is from 1/1 to 1/6 and water, water can be added so that it represents at least 50% by weight water. In one embodiment, the compositions comprise from 60% to 99% by weight of the perfumed composition.

The water added for the preparation of a perfumed composition can also contain additional ingredients as described below. The water phase is the preferred phase to incorporate the organic or inorganic base required to raise the pH of the final emulsion product.

Additional Ingredients

Other ingredients that may optionally be present in the compositions of the present invention include for example antioxidants, chelating agents, UV filters, active ingredients, moisturizers, humectants, emollients, colorants, dyes, antifoams and pH adjusting or buffering agents. These ingredients may be added at such point in the process as will be understood by skilled practitioners or as can be determined by a few simple experiments.

The amount of optional ingredients will vary depending on the purpose and effectiveness of the ingredient. Typically, such ingredients represent from 0.0005% to 3% by weight, preferably from 0.001% to 2% by weight, more preferably from 0.01% to 1% by weight, of the perfumed composition.

Method of Preparation of the Perfumed Compositions

The perfumed compositions according to the present invention may be prepared by any method known in the art, for example, by simple mixing at room temperature all the ingredients, for example by hand stirring or if need be, by mechanically mixing the components of the perfumed composition, and any optional components, to form a homogeneous mixture.

In one embodiment, the surfactants are added to the solvents (diols) with warming if necessary, and the mixture is stirred. Then the fragrances are added with stirring. The water phase is then added slowly to the organic phase with constant gentle stirring.

The pH is adjusted normally in the range 4.5 to 8.0, most preferably from 5.5 to 7.5, with the addition of typical inorganic alkaline materials like sodium and potassium hydroxides and with typical organic bases, mainly amines.

The preferred method consists in mixing at room temperature into a single phase the glycol(s), surfactants and fragrance oil, followed by the addition of water under agitation. High shear forces or other mechanical forces are not necessary to manufacture the present microemulsions. Optionally, the mixing of the solubilizers and glycols can be made at temperatures below 40° C., followed by cooling to about 25° C. prior to the incorporation of the fragrance to avoid the volatilization of some fragrances.

The preservative system and additives can be added to either the water or the oil phase or both based on their solubility. Finally, the pH is adjusted with an inorganic or organic base. A portion or the total amount of the base can be pre-added to the water phase Use of a Mixture of Non-ionic and Crypto Anionic Surfactant The present invention is also directed to the use of at least one crypto anionic surfactant and at least one nonionic surfactant having a molecular weight greater than 1700 containing at least 40% of ethylene oxide, to solubilize fragrances in an ethanol-free perfumed composition.

Kit

The ease of incorporation of the water phase makes it possible to market the invention in a kit form with instructions for the consumer prior to use. The kit would be made of an anhydrous system containing the fragrance and some or all of the ingredients of the solubilizer system, and a separated aqueous system containing the water and the rest of the ingredients. Such systems are also embodiments of the present invention, as they constitute starting material ingredients for the preparation of the compositions and microemulsions described in this specification.

In this respect, the present invention is also directed to an ethanol-free perfume product in a kit form comprising two compartments in which at least the following ingredients are divided:

a fragrance at least one crypto anionic surfactant, at least one ethoxylated non-ionic surfactant having a molecular weight greater than 1700 containing at least 40% of the ethylene oxide, at least one glycol having from 3 to 8 carbon atoms;

wherein the weight ratio of the fragrance to the surfactants and glycols is from 1/1 to 1/6, and water, wherein the compartment that contains the fragrance does not simultaneously contains the water.

The invention is also directed to an ethanol-free perfumed preparation, for example to be introduced in one compartment of said kit, comprising a fragrance and:

a) at least one crypto anionic surfactant, b) at least one ethoxylated non-ionic surfactant having a molecular weight greater than 1700 containing at least 40% of the ethylene oxide, d) at least one glycol having from 3 to 8 carbon atoms;

wherein the weight ratio of the fragrance to the surfactants and glycols is from 1/1 to 1/6.

A perfumed composition is thus obtainable by admixing in situ said ethanol-free perfumed preparation, and water.

The invention is illustrated by but not limited to the examples below.

EXAMPLES

Example 1

Table 1 shows the composition of a fragrance oil made of seven ingredients selected to represent various chemical families commonly used to prepare fragrances. Its main purpose is to show the effectiveness of the solubilizer system. It is not intended for olfactory attributes.

TABLE 1

| PERFUMERY NAME | % | CAS # | CHEMICAL GROUP |
|---|---|---|---|
| CIS 3 HEXENYL ACETATE | 15 | 3681-71-8 | Ester |
| METHYLIONONE GAMMA | 15 | 127-51-5 | Ionone |
| TRIPLAL | 15 | 68039-49-6 | Schiff base |

TABLE 1-continued

| PERFUMERY NAME | % | CAS # | CHEMICAL GROUP |
|---|---|---|---|
| ISO GAMMA SUPER | 10 | 68155-66-8 | Ketone |
| VANILINE | 15 | 121-33-5 | Aldehyde, hydroxyl, ether |
| TERPINEOL | 15 | 98-55-5 | Terpenic alcohol |
| PHENYL ETHANOL | 15 | 60-12-8 | Carbinol |

Example 2

Table 2 shows the composition of a fragrance oil made of fifteen ingredients selected to deliver, at a low concentration usage in the final water based perfume product, and a longevity of at least 8 hours. The fragrance is described having fruity freshness with notes of jasmine, violet and carnation.

TABLE 2

| PERFUMERY NAME | % | CAS # |
|---|---|---|
| UNDECALACTONE GAMMA | 0.5 | 104-67-6 |
| CIS 3 HEXENYL ACETATE | 1.0 | 3681-71-8 |
| HEXYLCINNAMIQUE ALDEHYDE | 12.0 | 101-86-0 |
| HEXENYLE CIS 3 BENZOATE | 2.0 | 25152-85-6 |
| EUGENOL | 2.0 | 97-53-0 |
| HELIONAL | 5.0 | 1205-17-0 |
| IONONE BETA | 3.0 | 14901-07-6 |
| METHYLIONONE GAMMA | 5.0 | 127-51-5 |
| BENZYL PROPIONATE | 1.0 | 122-63-4 |
| TRIPLAL | 0.5 | 68039-49-6 |

TABLE 2-continued

| PERFUMERY NAME | % | CAS # |
|---|---|---|
| BENZYLE ACETATE | 5.0 | 140-11-4 |
| HEDIONE HC | 30.0 | 24851-98-7 |
| ISO GAMMA SUPER | 26.0 | 68155-66-8 |
| Cis 3 HEXENYLE SALICYLATE | 5.0 | 65405-77-8 |
| VANILINE | 2.0 | 121-33-5 |

Examples 3 to 11

The compositions of Table 3 were prepared with fragrance oil 1 and are intended to illustrate the solubilizing power of the systems described in this specification. The samples were prepared mixing the surfactants, glycol and fragrance followed by the addition of water. The pH was adjusted to about 6.5 with a solution of 5% NaOH.

TABLE 3

| | Example # | | | | | | | | |
|---|---|---|---|---|---|---|---|---|---|
| | 3 | 4 | 5 | 6 | 7 | 8 | 9 | 10 | 11 |
| Fragrance of Example 1, % | 5 | 5 | 10 | 5 | 5 | 5 | 5 | 5 | 5 |
| CRYPTO-ANIONICS, % | | | | | | | | | |
| PPG-5 Ceteth-10 Phosphate (Crodaphos SG) | — | 1.5 | 3 | 1.5 | 1.5 | — | — | | — |
| Phenol-6EO Phosphate (Crodafos PH6A-LQ) | — | — | — | — | — | 1.5 | — | — | — |
| Oleth-10 Phosphate (Crodafos10A-SS) | | | | | | | | 2 | |
| Laureth-7 Citrate (Plantapon LC-7) | — | — | — | — | — | — | 2 | — | 2 |
| NON-IONIC, % | | | | | | | | | |
| PEG 40 Hydrogenated Castor Oil (Croduret 40 LD) | 5 | 5 | 10 | 5 | 5 | 5 | 5 | 7.5 | |
| Poloxamer 184 (Pluronic L64) | | | | | | | | | 5 |
| GLYCOLS, % | | | | | | | | | |
| Pentylene glycol | | | | | | | 5 | | |
| 1,2-Hexanediol | 5 | 5 | 10 | | | 5 | | | 5 |
| Dipropylene glycol | — | — | — | 5 | — | | — | 2.5 | — |
| Isopentyldiol | — | — | — | — | 5 | — | — | — | — |
| WATER, % | 85.0 | 83.5 | 60.0 | 83.5 | 83.5 | 83.5 | 83.0 | 83.0 | 83.0 |
| Surfactants/Glycol ratio | 1/1 | 1.3/1 | 1.3/1 | 1.3/1 | 1.3/1 | 1.4/1 | 1.3/1 | 3.8/1 | 1.3/1 |
| Fragrance/Solubilizer ratio | 1/2 | 1/2.3 | 1/2.3 | 1/2.3 | 1/2.3 | 1/2.3 | 1/2.4 | 1/2.4 | 1/2.4 |
| Appearance at 20° C. | Hazy | Clear | Clear | Clear | Clear | Clear | Clear | Clear | Clear |

The comparative composition of example 3 contains no crypto-anionic surfactant and it is hazy at 20° C. The compositions of examples 4 to 10 are clear and represent this invention containing a crypto-anionic surfactant neutralized to a pH near

Examples 12 to 19

The compositions of Table 4 were prepared with fragrance oil 2 and are intended to illustrate the solubilizing power of the systems described in this specification. The samples were prepared mixing the surfactants, glycol and fragrance followed by the addition of water. The pH was adjusted to about 6.5 with a solution of 5% NaOH.

TABLE 4

| | Example # | | | | | | | |
|---|---|---|---|---|---|---|---|---|
| | 12 | 13 | 14 | 15 | 16 | 17 | 18 | 19 |
| Fragrance of Example #2, % | 5 | 5 | 4 | 4 | 3 | 3 | 3 | 3 |
| CRYPTO-ANIONICS, % | | | | | | | | |
| PPG-5 Ceteth-10 Phosphate (Crodaphos SG) | | | 1.5 | | 1.5 | | | |
| Laureth-7 Citrate (Plantapon LC-7) | | 2 | | 2 | | 2 | 2 | 2 |
| NON-IONIC, % | | | | | | | | |
| PEG 40 Hydrogenated Castor Oil (Croduret 40 LD) | 9 | 7 | 7 | 7 | 7 | 7 | 5 | 5 |
| GLYCOLS, % | | | | | | | | |
| Pentylene glycol | | | | | | | 5 | |
| 1,2-Hexanediol | 3 | 3 | 3 | | | | | 5 |
| Dipropylene glycol | | | | 3 | | 3 | | |
| Isopentyldiol | | | | | 3 | | | |
| WATER, % | 80.0 | 83.0 | 84.5 | 85.0 | 83.5 | 85.5 | 85.0 | 85.0 |
| Surfactants/Glycol ratio | 3/1 | 3/1 | 2.8/1 | 3/1 | 2.8/1 | 3/1 | 1.4/1 | 1.4/1 |
| Fragrance/Solubilizer ratio | 1/2.4 | 1/2.4 | 1/2.8 | 1/3 | 1/3.8 | 1/4 | 1/4 | 1/4 |
| Appearance at 20° C. | Hazy | Clear | Clear | Clear | Clear | Clear | Clear | Clear |

The comparative composition of example 11 contains no crypto-anionic surfactant and it is hazy at 20° C. The compositions of examples 12 to 18 are clear and represent this invention containing a crypto-anionic surfactant neutralized to a pH near 6.5.

The invention claimed is:

1. An ethanol-free perfumed composition comprising a fragrance and:

a) at least one crypto anionic surfactant, said at least one crypto anionic surfactant being in a nonionic state at a pH below 3 and containing nonionic and anionic species as the pH increases such that at a pH required for the perfumed composition said at least crypto anionic surfactant has a mixture of nonionic and species, b) at least one ethoxylated nonionic surfactant having a molecular weight greater than 1700 containing at least 40% of ethylene oxide, d) at least one glycol having from 3 to 8 carbon atoms, and e) water;

wherein the weight ratio of the fragrance to the surfactants and glycols is from 1/1 to 1/6.

2. The composition according to claim 1, wherein the composition contains less than 3% of ethanol.

3. The composition according to claim 1, wherein the crypto anionic surfactant is flanked by a citrate or phosphate group or a mixture of them.

4. The composition according to claim 3 wherein the crypto anionic surfactant is derived from an ethoxylated non-ionic material having at least 30% of ethylene oxide attached to an alkyl, aryl, or propoxy chain or a mixture of them.

5. The composition according to claim 3, wherein the crypto anionic surfactant is selected from the group consisting of Laureth-7 Citrate, PPG-5-Ceteth-10 Phosphate, Phenol-6 EO Phosphate, and Oleth-10 Phosphate.

6. The composition according to claim 3, wherein the crypto anionic surfactant is neutralized with an inorganic or organic base to a pH below 8.

7. The composition according to claim 1, wherein the ethoxylated nonionic surfactant is an ethoxylated castor oil containing at least 40%.

8. The composition according to claim 1, wherein the ethoxylated nonionic surfactant is a block copolymer surfactant with a molecular weight from 2500 to 35000 and containing from 60% to 75% of ethylene oxide.

9. The composition according to claim 1, wherein the glycol has from 5 and 6 carbons.

10. The composition according to claim 1, wherein the at least one glycol is selected from the group consisting of pentylene glycol, isopentyldiol, 1,2-hexanediol, and dipropylene glycol and a mixture of the diols.

11. The composition according to claim 1, wherein the ratio by weight between the crypto anionic and nonionic surfactants is in the range of 1/1 to 1/7.

12. The composition according to claim 1, wherein the ratio by weight between the total surfactant content and the glycols is in the range of 4/1 to 1/1.

13. The composition according to claim 1, wherein the ratio by weight between the fragrance oil and the total content of surfactants and glycols is in the range of 1/1 to 1/6.

14. The composition according to claim 1, wherein the total weight content of the fragrances, surfactants and glycols in the composition is less than 40%.

15. A method for the preparation of a composition according to claim 1, wherein all the ingredients are mixed into a homogeneous system at temperatures not exceeding 40° C.

16. An ethanol-free perfumed preparation comprising a fragrance and:

a) at least one crypto anionic surfactant, said at least one crypto anionic surfactant being in a nonionic state at a pH below 3 and containing nonionic and anionic species as the pH increases such that at a pH required for the perfumed composition said at least crypto anionic surfactant has a mixture of nonionic and species, b) at least one ethoxylated nonionic surfactant having a molecular weight greater than 1700 containing at least 40% of the ethylene oxide, d) at least one glycol having from 3 to 8 carbon atoms;

wherein the weight ratio of the fragrance to the surfactants and glycols is from 1/1 to 1/6.

17. A perfumed composition obtainable by admixing in situ:

an ethanol-free perfumed preparation according to claim 16, and water.

18. An ethanol-free perfume product in a kit form comprising two compartments in which at least the following ingredients are divided:

a fragrance at least one crypto anionic surfactant, said at least one crypto anionic surfactant being in a nonionic state at a pH below 3 and containing nonionic and anionic species as the pH increases such that at a pH required for the perfumed composition said at least crypto anionic surfactant has a mixture of nonionic and species, at least one ethoxylated nonionic surfactant having a molecular weight greater than 1700 containing at least 40% of the ethylene oxide, at least one glycol having from 3 to 8 carbon atoms;

wherein the weight ratio of the fragrance to the surfactants and glycols is from 1/1 to 1/6, and water, wherein the compartment that contains the fragrance does not simultaneously contains the water.

19. The method for the preparation of a perfume product according to claim 18, wherein the content of each compartments are mixed.

20. The composition according to claim 6, wherein the crypto anionic surfactant is neutralized with an inorganic or organic base to a pH from 4.5 to 8.

* * * * *